United States Patent [19]

Skuballa et al.

[11] Patent Number: 4,894,391
[45] Date of Patent: Jan. 16, 1990

[54] PROSTACYCLIN DERIVATIVES, PROCESS FOR THE PREPARATION THEREOF, AND USE THEREOF AS MEDICINAL AGENTS

[75] Inventors: Werner Skuballa; Helmut Dahl; Bernd Radüchel; Helmut Vorbrüggen; Olaf Loge, all of Berlin, Fed. Rep. of Germany

[73] Assignee: Schering Aktiengesellschaft, Berlin and Bergkamen, Fed. Rep. of Germany

[21] Appl. No.: 623,869

[22] Filed: Jun. 25, 1984

[30] Foreign Application Priority Data

Jun. 23, 1983 [DE] Fed. Rep. of Germany ....... 3322893

[51] Int. Cl.⁴ .................. A61K 31/34; C07D 307/395
[52] U.S. Cl. ..................................... 514/452; 514/460; 514/461; 514/467; 549/214; 549/370; 549/414; 549/448; 549/465
[58] Field of Search ............... 549/370, 448, 465, 214, 549/414; 514/452, 460, 467, 461

[56] References Cited

U.S. PATENT DOCUMENTS 3,953,435  4/1976  Hayashi et al. ................. 260/468 D
4,219,479  8/1980  Vorbrüggen et al. .............. 424/263
4,364,951  12/1982 Skuballa et al. ..................... 424/263

FOREIGN PATENT DOCUMENTS 2088856  6/1982  United Kingdom ................ 549/465
0004201  11/1983 World Int. Prop. O. .......... 549/465

Primary Examiner—Nicky Chan
Attorney, Agent, or Firm—Millen, White & Zelano

[57] ABSTRACT

5-Cyanoprostacyclins of Formula I

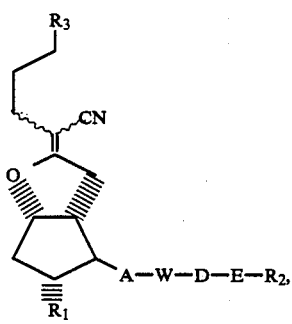

wherein
A is a —CH$_2$—CH$_2$—, trans—CH=CH—, or —C≡C-group,
W is a free or functionally modified hydroxymethylene group or a free or functionally modified

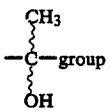

wherein the OH-group can be in the α- or β-position,
D and E together form a direct bond or
D is the group

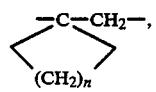

a straight-chain, saturated alkylene group of 1–5 carbon atoms, a branched, saturated or a straight-chain, unsaturated alkylene group of 2–5 carbon atoms, any of which can optionally be substituted by fluorine atoms,
n is the number 1, 2, or 3,
E is oxygen, sulfur, a —C≡C-bond, a direct bond, or a —CR$_4$=CR$_5$-group wherein R$_4$ and R$_5$ are different and can be a hydrogen atom or an alkyl group of 1–3 carbon atoms,
R$_2$ is an alkyl, cycloalkyl, optionally substituted aryl, or heterocyclic group,
R$_1$ is a free or functionally modified hydroxy group, and
R$_3$ is an acetal residue

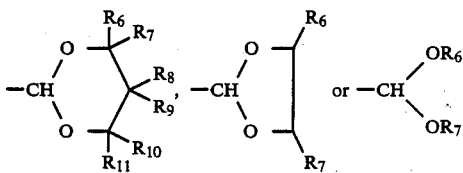

wherein R$_6$, R$_7$, R$_8$, R$_9$, R$_{10}$ and R$_{11}$ can be identical or different and each is a hydrogen atom or a straight-chain or branched alkyl group of 1–5 carbon atoms, or a substituted or unsubstituted phenyl residue,
have valuable pharmacological properties.

21 Claims, No Drawings

PROSTACYCLIN DERIVATIVES, PROCESS FOR THE PREPARATION THEREOF, AND USE THEREOF AS MEDICINAL AGENTS

BACKGROUND OF THE INVENTION

This invention relates to novel prostacyclin derivatives, a process for this preparation, as well as their use as medicinal agents.

It is known from the very voluminous state of the art of prostacyclins and their analogs that this class of compounds because of their biological and pharmacological properties, is suitable for the treatment of mammals, including man. However, their use meets with difficulties since they are chemically unstable and exhibit too brief a duration of activity for therapeutic purposes. All ongoing structural modifications are intended to increase the duration of activity as well as the selectivity of effectiveness.

In German Laid-Open Application DOS No. 2,753,244, (U.S. Pat. No. 4,219,479) prostacyclin derivatives are described which are stabilized by a nitrile group on the enol ether double bond. However, the properties of such compounds are still in need of improvement.

SUMMARY OF THE INVENTION

It is an object of this invention to provide improved compounds.

Upon further study of the specification and appended claims, further objects and advantages of this invention will become apparent to those skilled in the art.

It has now been found that a longer duration of activity and higher selectivity can be attained by substituting the 1-carboxy group in the 5-cyanoprostacyclins by an acetal group.

The resultant compounds of this invention are especially suited for inhibition of gastric acid secretion and for cytoprotection at the stomach, the heart, and the liver.

Consequently, these objects have been attained by providing 5-cyanoprostacyclins of Formula I

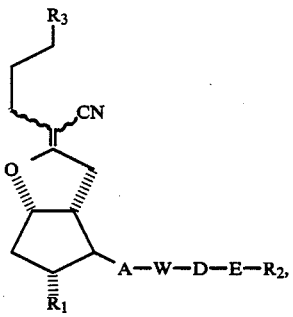

wherein
A is $-CH_2-CH_2-$, trans$-CH=CH-$, or $-C\equiv C-$;
W is a free or functionally modified hydroxymethylene group or a free or functionally modified

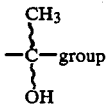group wherein the OH-group can be in the α- or β-position;
D and E together are a direct bond or
D is the group

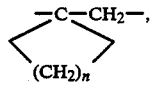

a straight-chain, saturated alkylene group of 1–5 carbon atoms, or a branched, saturated or a straight-chain, unsaturated alkylene group of 2–5 carbon atoms, any of which can optionally be substituted by fluorine atoms,
n is 1, 2, or 3,
E is oxygen, sulfur, a $-C\equiv C-$bond, a direct bond or a $-CR_4=CR_5-$group wherein $R_4$ and $R_5$ are different and can be hydrogen, halogen or an alkyl group of 1–3 carbon atoms,
$R_2$ is an alkyl, cycloalkyl, optionally substituted aryl, or heterocyclic group,
$R_1$ is a free or functionally modified hydroxy group, and
$R_3$ is an acetal residue

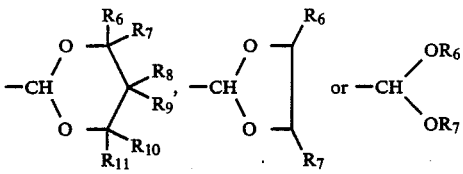

wherein $R_6$, $R_7$, $R_8$, $R_9$, $R_{10}$ and $R_{11}$ can be identical or different and each is hydrogen, or a straight-chain or branched alkyl group of 1–5 carbon atoms, or a substituted or unsubstituted phenyl residue.

DETAILED DISCUSSION

The compounds of Formula I include (5E) and (5Z) isomers.

The hydroxy groups $R_1$ and those in W can be functionally modified, for example by etherification and/or esterification wherein the free or modified hydroxy groups in W can be in the α- or β-position, free hydroxy groups being preferred.

Suitable ether and acyl residues are those residues known to a person skilled in the art. Readily cleavable ether residues are preferred, for example, the tetrahydropyranyl, tetrahydrofuranyl, e-ethoxyethyl, trimethylsilyl, dimethyl-tert-butylsilyl, and tribenzylsilyl residues. Examples of acyl residues include acetyl propionyl, butyryl, benzoyl or generally an acyl group of a $C_{1-15}$-hydrocarbon carboxylic or sulfonic acid.

As the alkyl group $R_2$, straight- or branched-chain, saturated and unsaturated alkyl residues (e.g., alkenyl) can be utilized, preferably saturated ones of 1–10, especially 1–7 carbon atoms which can be substituted, if desired, by optionally substituted aryl as defined below for $R_2$ per se. Examples include methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

The cycloalkyl group $R_2$ can contain 3–10, preferably 3–6 carbon atoms in the ring. The rings can be substituted by alkyl groups of 1–4 carbon atoms. Examples include cyclopropyl, cyclobutyl, cyclopentyl, cyclohexyl, methylcyclohexyl, and adamantyl.

Examples of substituted or unsubstituted aryl groups $R_2$ include: phenyl, 1-naphthyl and 2-naphthyl, each of which can be substituted by 1-3 halogen atoms, a phenyl group, 1-3 alkyl groups of 1-4 carbon atoms each, or a chloromethyl, fluoromethyl, trifluoromethyl, carboxy, $C_1$-$C_4$-alkoxy, or hydroxy group. Substitution in the 3- and 4-positions on the phenyl ring is preferred, for example by fluorine, chlorine, $C_1$-$C_4$-alkoxy, or trifluoromethyl, or in the 4-position by hydroxy.

Suitable heterocyclic groups $R_2$ include 5- and 6-membered heterocycles, usually aromatic, containing at least one hetero atom, preferably nitrogen, oxygen, or sulfur, the remainder being C-atoms. Examples include 2-furyl, 2-thienyl, 2-pyridyl, 3-pyridyl, 4-pyridyl, 3-furyl, 3-thienyl, etc.

Suitable alkylene groups D include straight-chain alkylene residues of 1-10 carbon atoms or branched-chain, saturated and unsaturated alkylene residues (alkylene, alkenylene) of 2-10 carbon atoms, preferably of 1-5 carbon atoms and 2-5 carbon atoms, respectively, all of which can optionally be substituted by fluorine atoms. Examples include: methylene, fluoromethylene, ethylene, 1,2-propylene, ethylethylene, trimethylene, tetramethylene, pentamethylene, 1-methyltetramethylene, 1-methyltrimethylene.

The alkyl groups $R_4$ and $R_5$ can be straight-chained or branched, saturated alkyl groups of 1-4 carbon atoms, e.g., as recited above for the $R_2$ alkyl groups. $R_4$ and $R_5$ as halogen can be chlorine and bromine, preferably chlorine.

The alkyl groups $R_6$, $R_7$, $R_8$, $R_9$, $R_{10}$, and $R_{11}$ can be straight-chain or branched, saturated alkyl groups of 1-5 carbon atoms, e.g., as mentioned above for $R_2$ as the alkyl group.

Suitable substituted phenyl residues for $R_6$ through $R_{11}$ include the substituted phenyl residues disclosed above for $R_2$.

This invention furthermore concerns a process for the preparation of the 5-cyanoprostacyclins of this invention according to Formula I, comprising conventionally subjecting a compound of Formula II

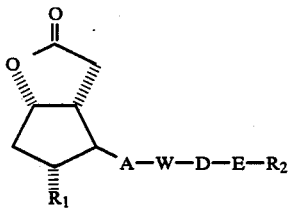

II wherein $R_1$, $R_2$, A, W, D, and E are as defined above, optionally after conventional protection of any free hydroxy groups present, to a water splitting-off step, after reaction with a carbanion produced from the nitrile of Formula III $$N\equiv C-CH_2-CH_2-CH_2-CH_2-R_3$$   III and a base such as lithium diisopropylamide, wherein $R_3$ is as defined above, optionally after liberation of protected hydroxy groups.

If desired, it is possible, in the thus-obtained products of the process or in the primary products of the organometallic reaction, in any desired sequence, to separate isomers, liberate protected hydroxy groups and/or esterify or etherify free hydroxy groups.

The reaction of the compound of Formula II with the organometallic compound, produced from the nitrile of Formula III and lithium diisopropylamide in ether-tetrahydrofuran mixtures, if desired in the presence of hexamethylphosphoric triamide, is performed preferably at $-50°$ C. to $-78°$ C. in a solvent or solvent mixture suitable for organometallic reactions, preferably diethyl ether or tetrahydrofuran.

Splitting off of water is accomplished according to methods known to a person skilled in the art, for example by reacting the products from the organometallic reaction with a catalytic amount of an acid in a water-immiscible solvent, such as toluene, benzene, methylene chloride, chloroform, carbon tetrachloride, diethyl ether, etc., preferably in toluene or in a water-binding solvent, e.g., acetic anhydride, at temperatures of $-20°$ C. to $100°$ C., preferably $0°-30°$ C. Examples of acids include p-toluenesulfonic acid, sulfuric acid, hydrochloric acid, boron trifluoride, etc. The functional modification of the free OH-groups takes place according to methods known to one skilled in the art. In order to introduce the ether blocking groups, for example, the reaction is carried out with dihydropyran or ethyl vinyl ether in methylene chloride, benzene, or chloroform with the use of an acidic catalyst, e.g., $POCl_3$, p-toluenesulfonic acid, or anhydrous mineral acids. The dihydropyran is used in excess, preferably in 2 to 10 times the amount required theoretically. The reaction is normally completed after 15-30 minutes at $0°-30°$ C.

The introduction of the acyl blocking groups takes place by conventionally reacting a compound of general Formula I with a carboxylic acid derivative, such as, for example, an acid chloride, acid anhydride, etc., in the presence of a tertiary amine base, such as, for example, pyridine, dimethylaminopyridine, etc.

A functionally modified OH-group can be liberated according to conventional methods to form the compounds of Formula I or the primary products of the organometallic reaction. For example, splitting off ether blocking groups is conducted in an aqueous solution of an organic acid, e.g., acetic acid, propionic acid, and others, or in an aqueous solution of an inorganic acid, such as, for example, hydrochloric acid. To enhance solubility, a water-miscible, inert organic solvent is suitably added. Organic solvents that can be used include, for example, alcohols, such as methanol and ethanol, and ethers, such as dimethoxyethane, dioxane, and tetrahydrofuran. Tetrahydrofuran is preferably employed. The splitting-off step is preferably conducted at temperatures of 20° to 80° C.

Splitting off the silyl ether blocking groups can take place, for example, with tetrabutylammonium fluoride or with KF in the presence of a crown ether. Examples of suitable solvents include tetrahydrofuran, diethyl ether, dioxane, methylene chloride, etc. The splitting-off step is preferably performed at temperatures of between 0° to 80° C.

The acyl groups can be saponified, for example, with alkali or alkaline earth metal carbonates or hydroxides in an alcohol or in the aqueous solution of an alcohol. Suitable alcohols include aliphatic alcohols, e.g., methanol, ethanol, butanol, etc., preferably methanol. Examples of alkali metal carbonates and hydroxides include potassium and sodium salts. Suitable alkaline earth metal carbonates and hydroxides include, for example, calcium carbonate, calcium hydroxide, and barium carbonate. The reaction takes place at −10° to 70° C., preferably at 25° C.

The nitriles of Formula I prepared according to this process include isomer mixtures with respect to the double bond neighboring the cyano group. These can be separated by customary separating methods, for example, column chromatography or layer chromatography.

The nitriles of Formula III utilized for the process can be conventionally prepared, for example, from the ester of 5-bromovaleric acid by reduction with diisobutyl aluminum hydride to form the 5-bromovaleraldehyde, acetalization with an alcohol or diol corresponding to the desired value of $R_3$, and subsequent reaction with potassium cyanide. The starting materials of Formula II are all well known and/or readily preparable using fully conventional methods starting from known or readily preparable starting materials.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials.

The compounds of this invention have cytoprotective and bronchodilatory activities. They are furthermore suited for inhibition of gastric acid secretion. Consequently, the novel prostacyclin derivatives of Formula I represent valuable pharmaceutically active agents for administration to mammals, including humans. Moreover, as compared with corresponding prostaglandins, they exhibit, with a similar spectrum of activity, a higher specificity and above all a substantially longer efficacy. As compared with $PGI_2$, they are distinguished by a greater stability. The high tissue specificity of the novel prostaglandins is demonstrated in a study on smooth-muscle organs, such as, for example, on the guinea pig ileum or on the isolated rabbit trachea, where a substantially lower stimulation can be observed than in the administration of natural prostaglandins of the E-, A-, or F-type.

The novel prostacyclin analogs exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thromboses, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas, antiallergic properties, lowering of pulmonary vascular resistance and pulmonary blood pressure, promotion of kidney blood flow, utilization in place of heparin or as an adjuvant in dialysis of hemofiltration, preservation of blood plasma stores, especially blood platelet stores, inhibition of labor, treatment of gestational toxicosis, enhancement of cerebral blood flow, etc. Besides, the novel prostacyclin derivatives exhibit antiproliferative and antidiarrheogenic properties. The prostacyclins of this invention also can be utilized in combination, for example, with β-blockers, diuretics, or phosphodiesterase inhibitors.

The dosage of the compounds is generally 1–1,500 µg/kg/day when administered to human patients. The unit dosage for the pharmaceutically acceptable formulation is generally 0.01–100 mg.

When administered by intravenous injection to nonanesthetized, hypertonic rats in doses of 5, 20, and 100 µg/kg body weight, the compounds of this invention exhibit a stronger blood-pressure-lowering effect and a more prolonged duration of efficacy than $PGE_2$ and $PGA_2$ without triggering diarrhea, as does $PGE_2$, or cardiac arrhythmias, as does $PGA_2$.

When administered by intravenous injection to narcotized rabbits, the compounds of this invention show, as compared with $PGE_2$ and $PGA_2$, a stronger and considerably prolonged blood-pressure-lowering effect without affecting other smooth-muscle organs or organ functions.

Sterile, injectable, aqueous or oily solutions are employable for parenteral administration. Suitable for oral administration are, for example, tablets, dragees, or capsules.

The invention accordingly also concerns medicinal agents based on the compounds of general Formula I and conventional auxiliary agents and excipients.

The active agents of this invention can be used, in conjunction with the auxiliary agents known and customary in galenic pharmacy, for example for the preparation of hypotensors.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup elixir or the like can be used wherein a sweetened vehicle is employed. Sustained release compositions can be formulated including those wherein the active compound is protected with differentially degradable coatings, e.g., microencapsulation, multiple coatings, etc.

The novel prostaglandin analogs of this invention are substantially more selective with regard to potency, as compared with known PG analogs in causing prostaglandin-like biological responses, and have a substantially longer duration of biological activity. Accordingly, each of these novel prostaglandins is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-Cyano-2-decarboxy-2-(5,5-dimethyl-1,3-dioxan-2-yl)-16-methylprostacyclin 13.47 g of diisopropylamine is combined at −25° C. within 15 minutes with 56.86 g of a 15% solution of butyllithium in hexane, and the mixture is agitated for one hour at −25° C. Then a solution of 26.27 g of 5-cyanovaleraldehyde neopentylacetal in 13.5 ml of tetrahydrofuran is added dropwise thereto at −76° C., the mixture is stirred for 20 minutes, and then a solution of 15 g of (1S,5R,6R,7R)-6-[(E)-(3S,4RS)-4-methyl-3-(tetrahydropyran-2-yloxy) - 1-octenyl]-7-(tetrahydropyran-2-yloxy)-2-oxabicyclo[3.3.0]octan-3-one in 11.3 ml of tetrahydrofuran and 11.3 ml of diethyl ether is added dropwise thereto. The mixture is agitated for 30 minutes at −76° C., the cooling bath is removed, the mixture is combined with saturated ammonium chloride solution, and acidified with 10% citric acid solution to pH 6. The mixture is extracted with a combination of ether/hexane (1+1), washed with water, dried with magnesium sulfate, and evaporated under vacuum. The residue is chromatographed on silica gel with hexane/ether (2+3), thus obtaining 18.05 g of the hydroxynitrile as a colorless oil which is agitated for 20 hours with 600 ml of a mixture of acetic acid/water/tetrahydrofuran at 22° C. The mixture is concentrated by evaporation at 30° C. with addition of toluene, and the residue is filtered on silica gel with ethyl acetate, thus producing 9.5 g of the 11,15-diol as a colorless oil.

To split off water and for acetylation, the above-produced compound is dissolved in 150 ml of toluene and 36 ml of acetic anhydride; 90 mg of p-toluenesulfonic acid is added and the mixture stirred for 2.5 hours at 20° C. Thereafter 130 ml of pyridine is added, the mixture is stirred for 6 hours at 20° C., diluted with water, extracted with toluene, washed with 10% citric acid solution and water, dried with magnesium sulfate, and evaporated under vacuum. The residue is chromatographed on silica gel with ether-hexane mixtures. Yield: 4.1 g of the desired (5E)-5-cyano-2-decarboxy-2-(5,5-dimethyl-1,3-dioxan-2-yl)-16-methylprostacyclin 11,15-diacetate, and also, as the more polar component, 3.5 g of the corresponding isomeric (5Z)-5-cyano-2-decarboxy-2-(5,5-dimethyl-1, 3-dioxan-2-yl)-16-methylprostacyclin 11,15-diacetate.

IR (CHCl$_3$): 2959, 2860, 2202, 1732, 1654, 1240, 972 cm$^{-1}$.

To split off the acetate, 4.1 g of the above-prepared diacetate is stirred in 220 ml of methanol with 5.3 g of potassium carbonate for 16 hours at 23° C. Then the mixture is concentrated under vacuum, diluted with ether, washed neutral with brine, dried over magnesium sulfate, and evaporated under vacuum. The residue is purified by chromatography on silica gel. With ethyl acetate/hexane (7+3) as the eluent, 3.4 g of the title compound is obtained as a colorless oil.

IR: 3600, 3430 (broad), 2957, 2860, 2200, 1649, 970 cm$^{-1}$.

5-Cyanovaleraldehyde neopentylacetal, employed in the synthesis, is prepared as follows:

5-Bromovaleraldehyde Neopentylacetal

Under argon and exclusion of water, 151.0 g of 5-bromovaleric acid methyl ester in 2,500 ml of toluene is combined at −65° to −70° C. dropwise with 840 ml of DIBAL-H solution (20% in toluene) and stirred for 20 minutes. In succession, 420 ml of isopropanol and 420 ml of water are added dropwise at −70° to −60° C. The mixture is allowed to warm up to 20° C. and agitated until the precipitate is readily filterable. The mixture is filtered, washed with toluene, and concentrated under vacuum to about 1,000 ml.

The resultant toluene solution of 5-bromovaleraldehyde is filled up to 1.28 l with toluene, combined with 120.8 g of 2,2-dimethyl-1, 3-propanediol and 1.28 g of p-toluenesulfonic acid hydrate, and refluxed on a water trap until separation of water is completed (1.5 hours). The mixture is allowed to cool, introduced into 435 ml of saturated NaHCO$_3$ solution, and the phases are separated. The toluene phase is washed three times with respectively 400 ml of water, dried with sodium sulfate, concentrated under vacuum, and then distilled in an oil pump vacuum, thus obtaining 154 g, bp 67° C. (0.7 mbar).

5-Cyanovaleraldehyde Neopentylacetal

Under argon, 150.0 g of 5-bromovaleraldehyde neopentylacetal is agitated in 600 ml of anhydrous dimethyl sulfoxide with 32.2 g of sodium cyanide for 3.5 hours at 90° C. The reaction solution is poured into 1,300 ml of water and extracted three times with respectively 500 ml of ether-hexane 1:1. The organic phases are washed five times with 120 ml of water, dried with sodium sulfate, concentrated under vacuum, and distilled in an oil pump vacuum, thus obtaining 100.1 g, bp 90° C. (0.6 mbar).

EXAMPLE 2

(5Z)-5-Cyano-2-decarboxy-2-(5,5-dimethyl-1,3-dioxan-2-yl)-16-methylprostacyclin 3.5 g of (5Z)-5-cyano-2-decarboxy-2-(5,5-dimethyl-1,3-dioxan-2-yl)-16-methylprostacyclin 11,15-diacetate (prepared according to Example 1) in 180 ml of methanol is agitated for 16 hours at 23° C. with 4.5 g of potassium carbonate. The mixture is then concentrated under vacuum, diluted with ether, washed neutral with brine, dried over magnesium sulfate, and evaporated under vacuum. The residue is purified by chromatography on silica gel. With ethyl acetate/hexane (7+3) as eluent, 2.8 g of the title compound is obtained as a colorless oil.

IR: 3600, 3420 (broad), 2958, 2860, 2200, 1650, 970 cm $^{-1}$.

EXAMPLE 3

5-Cyano-2-decarboxy-16, 16-dimethyl-2-(5,5-dimethyl-1,3-dioxan-2-yl)prostacyclin In analogy to Example 1, 3 g of (1S, 5R, 6R, 7R)-6-[(E)-(3R)-4,4-dimethyl-3-(tetrahydropyran-2-yloxy)-1-octenyl]-7-(tetrahydropyran-2-yloxy)-2-oxabicyclo[3.3.0]-octan-3-one, after chromatographic separation according to Example 1, yields 800 mg of the desired (5E)-5-cyano-2-decarboxy-16,16-dimethyl-2-(5,5-dimethyl-1,3-dioxan-2-yl)prostacyclin 11,15-diacetate and, as the more polar component, 650 mg of the corresponding isomeric (5Z)-5-cyano-2-decarboxy-16,16-dimethyl-2-(5,5-dimethyl-1,3-dioxan-2-yl)prostacyclin 11,15-diatetate.

IR: 2960, 2860, 2201, 1732, 1655, 1240, 972 cm $^{-1}$.

After splitting off the acetate residue according to Example 1, 620 mg of the title compound is obtained as a colorless oil.

IR: 3610, 3420 (broad), 2958, 2860, 2200, 1649, 970 cm $^{-1}$.

EXAMPLE 4

5-Cyano-2-decarboxy-2-(5,5-dimethyl-1,3-dioxan-2-yl)-16-phenoxy-17, 18, 19, 20-tetranorprostacyclin Analogously to Example 1, 4 g of (1S,5R,6R,7R)-6-—[(E)-(3R)-4-phenoxy-3-(tetrahydropyran-2-yloxy)-1-butenyl]-7-(tetrahydropyran-2-yloxy)-2-oxabicyclo[3.3.0]octan-3-one yields, after chromatographic separation (according to Example 1), 995 mg of the desired (5E)-5-cyano-2-decarboxy-2-(5,5-dimethyl-1,3-dioxan-2-yl)-16-phenoxy-17,18,19,20-tetranorprostacyclin 11,15-diacetate and, as the more polar component, 780 mg of the corresponding isomeric (5Z)-5-cyano-2-decarboxy-2-(5,5-dimethyl-1,3-dioxan-2-yl)-16-phenoxy-17,18,19,20-tetranorprostacyclin 11,15-diacetate.

IR: 2958, 2850, 2205, 1735, 1658, 1601, 1588, 1245, 976 cm $^{-1}$.

After cleavage of the acetate residues from the E isomer according to Example 1, 710 mg of the title compound is produced as a colorless oil.

IR: 3610, 3405 (broad), 2958, 2851, 2203, 1651, 1601, 1588, 974 cm $^{-1}$.

EXAMPLE 5

5-Cyano-2-decarboxy-2-(5,5-dimethyl-1, 3-dioxan-2-yl)-(15RS)-15-methylprostacyclin In analogy to Example 1, 2 g of (1S,5R,6R,7R)-6-[(E)-(3RS)-3-methyl-3-(tetrahydropyran-2-yloxy)-1-octenyl]-7-(tetrahydropyran-2-yloxy)-2-oxabicyclo[3.3.0]octan-3-one, after chromatographic separation according to Example 1, yields 530 mg of the desired (5E)-5-cyano-2-decarboxy-(5,5-dimethyl-1,3-dioxan-2-yl)-(15RS)-15-methylprostacyclin 11,15-diacetate and, as the more polar component, 432 mg of the corresponding isomeric (5Z)-5-cyano-2-decarboxy-2-(5,5-dimethyl-1,3-dioxan-2-yl)-(15RS)-15-methylprostacyclin 11,15-diacetate.

IR: 2955, 2858, 2200, 1738, 1652, 1245, 976 cm $^{-1}$.

After splitting off the acetate residues from the E isomer according to Example 1, 395 mg of the title compound is obtained as a colorless oil.

IR: 3605, 3410 (broad), 2957, 2860, 2201, 1651, 974 cm $^{-1}$.

EXAMPLE 6

5-Cyano-2-decarboxy-2-(5,5-dimethyl-1,3-dioxan-2-yl)-(16RS)-16-methyl-18,18,19,19-tetradehydroprostacyclin Analogously to Example 1, 2.85 g of (1S,5R,6R,7R)-6-[(E)-(3S,4RS)-4-methyl-3-(tetrahydropyran-2-yloxy)-1-octen-6-ynyl]-7-(tetrahydropyran-2-yloxy)-2-oxabicyclo[3.3.0]-octan-3-one yields, after chromatographic separation according to Example 1, 760 mg of the desired (5E)-5-cyano-2-decarboxy-2-(5,5-dimethyl-1,3-dioxan-2-yl)-(16RS)-16-methyl-18,18,19,19-tetradehydroprostacyclin 11,15-diacetate and, as the more polar component, 625 mg of the corresponding isomeric (5Z)-5-cyano-2-decarboxy-2-(5,5-dimethyl-1,3-dioxan-2-yl)-(16RS)-16-methyl-18,18,19,19-tetradehydroprostacyclin 11,15-diacetate.

IR: 2962, 2858, 2206, 1735, 1651, 1248, 976 cm $^{-1}$.

After cleavage of the acetate residues from the E isomer according to Example 1, 585 mg of the title compound is obtained as a colorless oil.

IR: 3604, 3410 (broad), 2959, 2857, 2204, 1652, 974 cm $^{-1}$.

EXAMPLE 7

5-Cyano-2-decarboxy-2-(5,5-dimethyl-1, 3-dioxan-2-yl)-(16RS)-16,20-dimethyl-18,18,19,19-tetradehydroprostacyclin In analogy to Example 1, 3 g of (1S,5R,6R,7R)-6-[(E)-(3S,4RS)-4-methyl-3-(tetrahydropyran-2-yloxy)-1-nonen-6-ynyl]-7-(tetrahydropyran-2-yloxy)-2-oxabicyclo[3.3.0]octan-3-one yields, after chromatographic separation as in Example 1, 775 mg of the desired (5E)-5-cyano-2-decarboxy-2-(5,5-dimethyl-1,3-dioxan-2-yl)-(16RS)-16,20-dimethyl-18,18,19,19-tetradehydroprostacyclin 11,15-diacetate and, as the more polar component, 630 mg of the corresponding isomeric (5Z)-5-cyano-2-decarboxy-2-(5,5-dimethyl-1, 3-dioxan-2-yl)-(b 16RS)-16,20-dimethyl-18,18,19,19-tetradehydroprostacyclin 11,15-diacetate.

IR: 2960, 2862, 2202, 1735, 1656, 1248, 974 cm $^{-1}$.

After splitting off the acetate residues from the E isomer according to Example 1, 590 mg of the title compound is obtained as a colorless oil.

IR: 3600, 3420 (broad), 2960, 2858, 2202, 1655, 974 cm $^{-1}$.

EXAMPLE 8

5-Cyano-2-decarboxy-2-(1, 3-dioxolan-2-yl)-(16RS)-16-methylprostacyclin 13.47 g of diisopropylamine is combined at −25° C. within 15 minutes with 56.86 g of a 15% solution of butyllithium in hexane. After one hour, a solution of 20.67 g of 5-cyanovaleraldehyde diethyleneacetal in 12 ml of tetrahydrofuran is added dropwise thereto at −76° C., the mixture is stirred for 20 minutes and then a solution of 6.26 g of (1S,5R,6R,7R)-6-[(E)-(3S,4RS)-3-hydroxy-4-methyl-1-octenyl]-7-hydroxy-2-oxabicyclo[3.3.0]octan-3-one in 12 ml of tetrahydrofuran and 12 ml of diethyl ether is added dropwise thereto. The mixture is stirred for 30 minutes at −76° C., the cooling bath is removed, the mixture is combined with saturated ammonium chloride solution, and then acidified with 10% citric acid solution to pH 6. The mixture is extracted with a mixture of diethyl ether/hexane (1+1), washed with water, dried with magnesium sulfate, and evaporated under vacuum. The residue is chromatographed on silica gel with hexane/diethyl ether (1/9), thus obtaining 7 g of the hydroxynitrile as a colorless oil; the latter, to split off water, is dissolved in 120 ml of toluene, combined with 70 mg of p-toluenesulfonic acid, and stirred for 2 hours at 20° C. Subsequently the mixture is washed with sodium bicarbonate and water, dried over magnesium sulfate, and evaporated under vacuum. The residue is chromatographed on silica gel with hexane and a rising ethyl acetate proportion, thus obtaining as the more polar component 2.30 g of (5Z)-5-cyano-2-decarboxy-2-(1, 3-dioxolan-2-yl)-(16RS)-16-methylprostacyclin and 3.01 g of the title compound (5E isomer) as a colorless oil.

IR: 3600, 3420 (broad), 2955, 2858, 2207, 1653, 974, 948 cm $^{-1}$.

5-Cyanovaleraldehyde diethyleneacetal, used for the synthesis, is prepared as follows:

(8a) 5-Bromovaleraldehyde

At −70° C., 271 ml of a 1.2-molar solution of diisobutyl aluminum hydride in toluene is added dropwise under agitation to a solution of 48.75 g of the methyl ester of bromovaleric acid in 2.5 of toluene. The mixture is stirred for another 30 minutes and then, in succession, 50 ml of isopropyl alcohol and 135 ml of water are added dropwise, and the mixture is agitated for 2 hours at room temperature, filtered off from the precipitate, and evaporated under vacuum, thus obtaining 43 g of 5-bromovaleraldehyde which is further reacted without purification.

(8b) 5-Bromovaleraldehyde Diethyleneacetal 43 g of 5-bromovaleraldehyde, 51 ml of ethylene glycol, 500 mg of p-toluenesulfonic acid, and 1 l of toluene are heated for 6 hours under reflux with a water trap. After cooling, the mixture is shaken with sodium bicarbonate solution and brine, dried over magnesium sulfate, and the toluene is distilled off under vacuum. The liquid residue is distilled at 0.2 mbar, thus obtaining 25.06 g with a boiling point of 64° C.

(8c) 5-Cyanovaleraldehyde Diethyleneacetal

Under argon, 32.7 g of 5-bromovaleraldehyde diethyleneacetal is agitated at 90° C. in 140 ml of dimethyl sulfoxide with 16.24 g of sodium cyanide for 6 hours. The mixture is cooled off, diluted with 300 ml of water, extracted repeatedly with diethyl ether/hexane (1:1), the extract is washed with brine, dried over magnesium sulfate, and the solvent is removed by evaporation under vacuum. The liquid residue is distilled at 0.8 mbar, thus obtaining 16.6 g, bp 87° C.

EXAMPLE 9

5-Cyano-2-decarboxy-2-(1,3-dioxolan-2-yl)-16,16-dimethylprostacyclin

Analogously to Example 8, 700 mg of (1S,5R,6R,7R)-6-[(E)-(3S)-4,4-dimethyl-3-(tetrahydropyran-2-yloxy)-1-octenyl]-7-(tetrahydropyran-2-yloxy)-2-oxabicyclo[3.3.0]-octan-3-one yields 310 mg of the title compound as a colorless oil.

IR: 3600, 3410 (broad), 2960, 2861, 2203, 1649, 975, 948 cm $^{-1}$.

EXAMPLE 10

5-Cyano-2-decarboxy-2-diethoxymethyl-(16RS)-16-methylprostacyclin

At −25° C., 1.347 g of diisopropylamine is combined within 15 minutes with 5.686 g of a 15% solution of butyllithium in hexane. After one hour, a solution of 2.47 g of 5-cyanovaleraldehyde diethylacetal in 15 ml of tetrahydrofuran is added dropwise thereto at −76° C., the mixture is stirred for 20 minutes, and then a solution of 630 mg of (1S,5R,6R,7R)-6-[(E)-(3S,4RS)-3-hydroxy-4-methyl-1-octenyl]-7-hydroxy-2-oxabicyclo[3.3.0]octan-3-one in 3 ml of tetrahydrofuran and 3 ml of diethyl ether is added dropwise thereto. The mixture is agitated for 30 minutes at −76° C., the cooling bath is removed, the mixture is combined with saturated ammonium chloride solution and extracted with diethyl ether/hexane (1:1), washed with brine, dried over magnesium sulfate, and evaporated under vacuum. The residue is chromatographed on silica gel with hexane/diethyl ether (1/9), thus obtaining 720 mg of the hydroxynitrile as a colorless oil. This compound is dissolved in 15 ml of toluene to split off water and stirred for 2 hours at 20° C. with 10 mg of ptoluenesulfonic acid. Then the mixture is diluted with diethyl ether, shaken with sodium bicarbonate solution and water, dried over magnesium sulfate, and evaporated under vacuum. The residue is chromatographed on silica gel with hexane/ethyl acetate (¼), thus producing as the more polar component 200 mg of (5Z)-5-cyano-2-decarboxy-2-diethoxymethyl-(16RS)-16-methylprostacyclin and 305 mg of the title compound (5E isomer) as a colorless oil.

IR: 3605, 3410 (broad), 2959, 2860, 2201, 1650, 976 cm $^{-1}$.

5-Cyanovaleraldehyde diethylacetal, employed for the synthesis, is obtained analogously to Example 8c from 5-bromovaleraldehyde diethylacetal [Bull. Chem. Soc. Jp. 49 : 1989 (1976)] by reaction with sodium cyanide; bp 82° C. at 0.7 mbar.

EXAMPLE 11

5-Cyano-2-decarboxy-2-(5,5-dimethyl-1,3-dioxan-2-yl)-(16S)-16-methylprostacyclin At −25° C., 8.76 g of diisopropylamine is combined with 73 ml of a 1.2-molar solution of butyllithium in hexane. After one hour, a solution of 17.08 g of 5-cyanovaleraldehyde neopentylacetal in 8 ml of tetrahydrofuran is added dropwise at −78° C. After 20 minutes, a solution of 9.75 g of (1S,5R,6R,7R)-6-[(E)-(3S,4S)-4-methyl-3-(tetrahydropyran-2-yloxy)-1-octenyl]-7-(tetrahydropyran-2-yloxy)-2-oxabicyclo[3.3.0]octan-3-one (see J. Org. Chem. 38: 1250 [1979]) in 8 ml of tetrahydrofuran and 8 ml of diethyl ether is added dropwise thereto. After another 30 minutes at −78° C., the mixture is combined with saturated ammonium chloride solution and acidified with citric acid to pH 6, then extracted with ether/hexane (1+1), washed with water, dried over magnesium sulfate, and evaporated under vacuum. The residue is chromatographed with hexane/ether (2+3) on silica gel, thus obtaining 12 g of the hydroxynitrile as an oil. To split off the tetrahydropyranyl ether blocking groups, the product is agitated for 24 hours with 400 ml of a mixture of acetic acid/water/tetrahydrofuran (65/35/10), evaporated under vacuum, and the residue is filtered with hexane/ethyl acetate (2+8) over silica gel. Yield: 6 g of the 11,15-diol as a colorless oil.

To split off water and to perform acetylation, the oil is dissolved in 100 ml of toluene and 23 ml of acetic anhydride, 60 mg of p-toluenesulfonic acid is added, and the mixture is stirred for 3 hours at 20° C. Thereafter the mixture is combined with 8 ml of pyridine. After another 6 hours, the mixture is diluted with water, extracted with toluene, washed with 10% citric acid solution and water, dried with magnesium sulfate, and evaporated under vacuum. The residue is chromatographed on silica gel with ether/hexane (1+1), thus obtaining 2.60 g of the desired (5E)-5-cyano-2-decarboxy-2-(5,5-dimethyl-1,3-dioxan-2-yl)-(16S)-16-methylprostacyclin 11,15-diacetate and, as the more polar component, 2.20 g of the corresponding isomeric (5Z)-5-cyano-2-decarboxy-2-(5,5-dimethyl-1,3-dioxan-2-yl)-(16S)-16-methylprostacyclin 11,15-diacetate.

IR (5E Isomer): 2960, 2861, 2202, 1735, 1655, 976 cm$^{-1}$.

To split off the acetate, 2.60 g of the above-prepared (5E)-11,15-diacetate is stirred in 140 ml of methanol with 3.45 g of potassium carbonate for 16 hours at 20° C. To work up the mixture, it is concentrated under vacuum, diluted with ether, washed with brine, dried over magnesium sulfate, and evaporated under vacuum. The residue is purified by chromatography on silica gel with hexane/ethyl acetate (3+7), thus obtaining 2.19 g of the title compound as a colorless oil.

IR: 3600, 3420 (broad), 2958, 2861, 2203, 1651, 974 cm$^{-1}$.

EXAMPLE 12

5-Cyano-2-decarboxy-2-(5,5-dimethyl-1,3-dioxan-2-yl)-(16R)-16-methylprostacyclin Analogously to Example 11, but using the other 16-epimer, 5 g of (1S,5R,6R,7R)-6-[(E)-(3S,4R)-4-methyl-3-(tetrahydropyran-2-yloxy)-1-octenyl]-7-(tetrahydropyran-2-yloxy)-2-oxabicyclo[3.3.0]octan-3-one (see J. Org. Chem. 38: 1250 [1973]) yields 1.15 g of the title compound as an oil.

IR: 3600, 3420 (broad), 2959, 2861, 2202, 1650, 974 cm$^{-1}$.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 5-cyanoprostacyclin of the formula

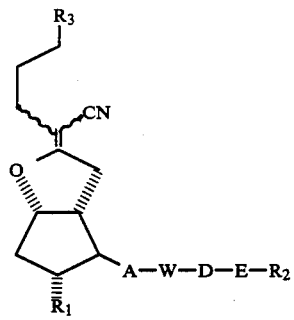

wherein

A is a $-CH_2-CH_2-$, trans-$CH=CH-$, or $-C\equiv C-$;

W is hydroxymethylene, RO-methylene, or

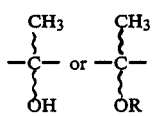

wherein the OH- or OR-group can be in the α- or β-position;

R is tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid;

D and E together are a direct bond, or

D is

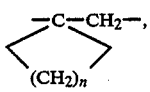

a straight-chain-$C_{1-5}$-alkylene group or a branched- or straight-chain, -alkylene, -alkenylene or group of 2–5 carbon atoms, or one of these groups substituted by fluorine and E is oxygen, sulfur, $-C\equiv C-$, a direct bond, or $-CR_4=CR_5-$ wherein $R_4$ and $R_5$ are different and each is hydrogen, halogen or alkyl of 1–4 carbon atoms;

n is 1, 2, or 3;

$R_2$ is (a) $C_{1-10}$ alkyl or alkenyl; (b) $C_{1-10}$ alkyl or alkenyl, each substituted by $C_{6-10}$ aryl or by $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; (c) $C_{3-10}$ cycloalkyl, (d) $C_{3-10}$ cycloalkyl substituted by $C_{1-4}$ alkyl, (e) $C_{6-10}$ aryl, (f) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one of which is O, N or S, the remainder being carbon atoms;

$R_1$ is OH or OR; and $R_3$ is

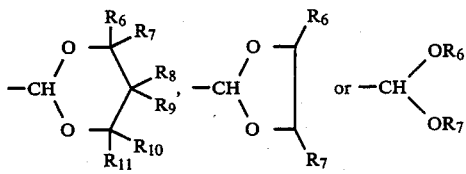

wherein R6, R7, R8, R9, R10, and R11 can be identical or different and each is hydrogen, $C_{1-5}$-alkyl, $C_{6-10}$ aryl, or $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group.

2. A compound of claim 1, wherein $R_3$ is

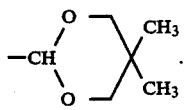

3. A compound of claim 1, wherein the 16-position is substituted by 1 or 2 —CH3 groups.

4. A compound of claim 1, wherein $AWDER_2$ is

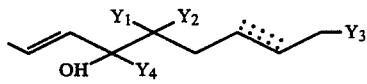

wherein $Y_1$, $Y_2$, $Y_3$, and $Y_4$ each independently is H, $CH_3$ or $C_2H_5$.

5. A compound of claim 1, wherein $AWDER_2$ is

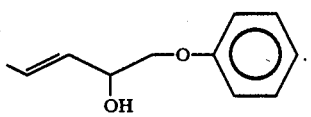

6. 5-Cyano-2-decarboxy-2-(5,5-dimethyl-1,3-dioxan-2-yl)-16-methylprostacyclin, a compound of claim 1.

7. (5Z)-5-Cyano-2-decarboxy-2-(5,5-dimethyl-1,3-dioxan-2-yl)-16-methylprostacyclin, a compound of claim 1.

8. 5-Cyano-2-decarboxy-16,16-dimethyl-2-(5,5-dimethyl-1,3-dioxan-2-yl)prostacyclin, a compound of claim 1.

9. 5-Cyano-2-decarboxy-2-(5,5-dimethyl-1,3-dioxan-2-yl)-16-phenoxy-17,18,19,20-tetranorprostacyclin, a compound of claim 1.

10. 5-Cyano-2-decarboxy-2-(5,5-dimethyl-1,3-dioxan-2-yl)-(15RS)-15-methylprostacyclin, a compound of claim 1.

11. 5-Cyano-2-decarboxy-2-(5,5-dimethyl-1,3-dioxan-2-yl)-(16RS)-16-methyl-18,18,19,19-tetradehydroprostacyclin, a compound of claim 1.

12. 5-Cyano-2-decarboxy-2-(5,5-dimethyl-1,3-dioxan-2-yl)-(16RS)-16,20-dimethyl-18,18,19,19-tetradehydroprostacyclin, a compound of claim 1.

13. 5-Cyano-2-decarboxy-2-(1,3-dioxolan-2-yl)-(16RS)-16-methylprostacyclin, a compound of claim 1.

14. 5-Cyano-2-decarboxy-2-(1, 3-dioxolan-2-yl)-16,16-dimethylprostacyclin, a compound of claim 1.

15. 5-Cyano-2-decarboxy-2-diethoxymethyl-(16RS)-16-methylprostacyclin, a compound of claim 1.

16. 5-Cyano-2-decarboxy-2-(5,5-dimethyl-1,3-dioxan-2-yl)-(16S)-16-methylprostacyclin, a compound of claim 1.

17. 5-Cyano-2-decarboxy-2-(5,5-dimethyl-1,3-dioxan-2-yl)-(16R)-16-methylprostacyclin, a compound of claim 1.

18. A pharmaceutical composition comprising an effective amount of a compound of claim 1 and a pharmacologically acceptable carrier.

19. A composition of claim 18, wherein the amount of said compound is 0.01–100 mg.

20. A method of inhibiting gastric acid secretion or for cytoprotection in a patient comprising administering an effective amount of a compound of claim 1 to the patient.

21. A method for achieving an effect in a patient comprising administering an effective amount of a compound of claim 1 to the patient wherein the effect is lowering of peripheral arterial or coronary vascular resistance, inhibition of thrombocyte aggregation or dissolution of platelet thrombi, myocardial cytoprotection and thus lowering of systemic blood pressure without simultaneously lowering stroke volume and coronary blood flow; treatment for stroke, prophylaxis or therapy of coronary heart disease, coronary thromboses, cardiac infarction, peripheral arterial diseases, arteriosclerosis or thrombosis, prophylaxis and therapy of ischemic attacks of the CNS system, therapy for shock, inhibition of bronchoconstriction, inhibition of gastric acid secretion, cytoprotection for gastric or intestinal mucosa, cytoprotection in the liver or pancreas, antiallergic treatment, lowering of pulmonary vascular resistance or pulmonary blood pressure, promotion of kidney blood flow, utilization in place of heparin or as an adjuvant in dialysis of hemofiltration, preservation of blood plasma stores, inhibition of labor, treatment of gestational toxicosis, enhancement of cerebral blood flow, or treatment for antiproliferative or antidiarrheogenic purposes.

* * * * *